US008424524B2

(12) United States Patent
Heinonen

(10) Patent No.: US 8,424,524 B2
(45) Date of Patent: Apr. 23, 2013

(54) METHOD AND APPARATUS FOR PRODUCING AN AVERAGE SIGNAL CHARACTERISTIC PROFILE FROM CYCLICALLY RECURRING SIGNALS

(75) Inventor: Erkki Heinonen, Helsinki (FI)

(73) Assignee: General Electric Company, Schenectady, NY (US)

( * ) Notice: Subject to any disclaimer, the term of this patent is extended or adjusted under 35 U.S.C. 154(b) by 1636 days.

(21) Appl. No.: 11/292,956

(22) Filed: Dec. 2, 2005

(65) Prior Publication Data

US 2007/0125378 A1    Jun. 7, 2007

(51) Int. Cl.
*A61M 11/00* (2006.01)
*A61M 16/00* (2006.01)
*A61B 5/02* (2006.01)
*A61B 5/08* (2006.01)

(52) U.S. Cl.
USPC ............ 128/204.23; 128/204.18; 128/204.21; 128/204.26; 128/920; 128/923; 600/483; 600/484; 600/526; 600/532

(58) Field of Classification Search .................. 128/920, 128/923, 204.18, 204.21, 204.23, 204.26; 600/484, 526, 532, 204.23, 483
See application file for complete search history.

(56) References Cited

U.S. PATENT DOCUMENTS 5,971,934 A * 10/1999 Scherer et al. ................ 600/526
6,099,481 A    8/2000 Daniels et al.

OTHER PUBLICATIONS

European search report dated Jun. 27, 2007.

* cited by examiner

*Primary Examiner* — Patricia Bianco
*Assistant Examiner* — Nihir Patel
(74) *Attorney, Agent, or Firm* — Andrus, Sceales, Starke & Sawall, LLP

(57) ABSTRACT

A method and apparatus for providing an average signal characteristic profile derived from signals obtained from different cycles of a cyclically recurring physiological phenomenon. A signal produced from first and second cycles of the physiological phenomenon is sampled at a series of data points to obtain second physiological property values at the data points. The change in the second physiological property values for the first cycle signal between a pair of successive data points and the change in the second physiological property values for the second cycle signal between the same pair of successive data points are determined and averaged. The average change amount is applied to a value of the average signal characteristic profile at one of the pair of successive data points to produce a new second physiological property value for the average signal characteristic profile at the other of the data points of the pair.

12 Claims, 4 Drawing Sheets

METHOD AND APPARATUS FOR PRODUCING AN AVERAGE SIGNAL CHARACTERISTIC PROFILE FROM CYCLICALLY RECURRING SIGNALS

FIELD OF THE INVENTION

The present invention relates to a method and apparatus for producing an average signal characteristic profile from cyclically recurring signals.

BACKGROUND OF THE INVENTION

Physiological signals often appear as a sum of complicated processes of various affecting variables. A physiological signal may also be cyclical, i.e. repeating itself with respect to some of the variables. As a result of the foregoing, each single cycle of the signal carries information of a physiological phenomenon, but the physiological signal will differ from cycle-to-cycle due to variations in other affecting variables. A problem with such signals is that single cycle information may be noisy or may reflect only a short temporary state, whereas the extraction of useful clinical information may require signal averaging over a longer period of time and over multiple cycles.

Breathing is an example of such a cyclic process. Breathing comprises the inspiration and expiration phases of a respiratory cycle. Every breath can be characterized with different variables such as breath volume or duration and time division ratio between inspiration and expiration. A given breath may also affect subsequent breaths. In spontaneous breathing these variables may distribute to a broad range of values and successive breaths may be very different from each other.

Breathing gas composition is also characterized with different variables. Inspired breathing gases are typically a mixture of oxygen and nitrogen, i.e. air. In the lungs, oxygen is taken up into circulating blood and carbon dioxide ($CO_2$) is released from the blood to the breathing gases in the lungs. Thus, the expired breathing gases also include $CO_2$. Expiration gas composition varies in the course of expiration. At the beginning of expiration, the expired gases comprise mainly the inspiration breathing gases remaining in the airways at the end of the previous inspiration. Subsequently expired breathing gases comprise gases from the alveolar portions of the lungs. The alveolar gas $CO_2$ concentration is a flow-weighted average of the gas concentrations from different lung regions. Flow rates from the lung regions vary according to variations in local pressure, compliance, and flow resistance. These determine the ventilation of a region of the lungs. Regional gas composition depends on the ratio of ventilation and blood perfusion of the region. The higher the rate of change of the gases in the gas space of a region (ventilation) and the lower the blood perfusion passing through the region, the lower the $CO_2$ concentration and the higher the oxygen concentration in the gases will be. The regional expiration flow rate, as well as the ventilation/perfusion ratio, varies in different lung-related sicknesses. The resulting expiration gas composition profile over the course of expiration is thus characteristic for these sicknesses, and this profile can be used for diagnostic purposes.

Capnography measures breathing gas $CO_2$ concentrations. In routine bedside use, the concentration is measured over time showing a pattern of breathing respiratory cycles divided into inspiration and expiration phases. By combining capnographic measurement during expiration with a spirometric measurement of breath volume, a volumetric capnograph (VCap) may be generated. Such a capnograph is a signal profile relating $CO_2$ concentrations to expired breathing gas volume.

VCap has been combined with a measurement of arterial blood $CO_2$ partial pressure ($PaCO_2$) obtained from a blood sample using a blood gas analyzer. In an ideal lung without shunt and alveolar dead-space, a $CO_2$ measurement at the end of expiration, i.e. an end tidal $CO_2$ measurement ($EtCO_2$), is very close to $PaCO_2$. However, in various sicknesses the $PaCO_2$-$EtCO_2$ difference increases. The slope of the VCap alveolar expiration curve may also increase. For comparison, arterial sampling and the expiration breathing pattern have to be coincidental. Blood transit time from the lungs to arteries reachable for sampling is about 10-20 seconds. During this period, a couple of breaths variable in volume and duration may occur. This results in variations in dissolved gas concentrations in the blood. There may also be significant gas composition variations between successive breaths. To be able to compare the arterial dissolved gas concentrations with those of the breathing gases, the signals corresponding to the measured quantities have to be averaged over a period of time sufficient to even out the cyclical signal variations.

A problem in extracting a characteristic gas concentration profile from cyclically variable signals obtained during expiration is presented in FIG. 1 showing a simplified example of signals from two expirations in solid black lines. The two expirations vary in volume. A first of the breaths marked with (x) and reference number 10 is about 430 mL in volume and the second marked with (o) and reference numeral 12 is about 600 mL. Such variation is commonly found in spontaneous breathing. A characteristic for the smaller volume breath 10 is a higher expiration $CO_2$ concentration profile compared to that of the larger volume breath 12. $CO_2$ concentration is shown on the abscissa, scaled in $CO_2$ partial pressure ($PCO_2$) in millimeters of mercury (mmHg). A large expiration is typically preceded by a large inspiration that dilutes the alveolar gas concentration more effectively, resulting in a lower $CO_2$ concentration profile for expiration 12. Assuming the arterial blood is sampled during these two breaths, an average $CO_2$ reading of the breaths from which the cyclic variation shown in FIG. 1 has been eliminated is needed for comparing the blood and breathing gas $CO_2$ concentrations for diagnostic purposes.

In FIG. 1, the solid line 14 represents the average calculated for expirations 10 and 12 for each increment of volume extending along the abscissa. At 430 ml the small volume breath 10 ends and the rest of the average curve up to the volume of the larger breath 12 follows the larger breath. At the end of smaller breath a distortion occurs in the average curve 14. This distortion reflects the difference in expired breathing gases volumes rather than the $CO_2$ concentration properties of the expiration. Thus the slope calculated for the VCap alveolar expiration curve does not reflect the true lung expiration profile. Also the tidal volume ($V_T$) and breath end-tidal $CO_2$ ($EtCO_2$) concentration will be misleading for comparison to the arterial $CO_2$ ($PaCO_2$).

SUMMARY OF THE INVENTION

The present invention relates to the analysis of cyclical physiological signals, successive cycles of which carry along one or more variations not directly related to the physiological property of interest. More particularly, this invention presents a method to, in effect, filter out a cyclic variation from the physiological signal. With the method, an averaged signal representing a characteristic profile of the cyclic signal is thus achieved.

To this end, the present invention presents what may be characterized as a derivative-filter technique. When applied to the analysis of expired breathing gases, the invention is based on the principle that every expiration $CO_2$ volume profile correctly presents the characteristic lung ventilation-perfusion profile under the prevailing circumstances of patient physiology, breathing pattern, and breath gas volume. Breathing gas expirations correctly reflect the $CO_2$ gradients under the prevailing circumstances, which may still be very different from each other, varying by length along abscissa and height along the ordinate when graphed as shown in FIG. 1. However, each point of the curve of such a graph represents a flow-weighted sum of the gas composition within different alveolar regions of the lungs.

While the flow weighting depends on the regional pressure and flow resistance characteristics, regional gas composition depends on the ventilation/perfusion (V/Q) relationship. These mixing factors determine the regional gas mixture composition. When measuring the gas mixture composition at two successive time events or data points, the change between them represents the change in the mixing factors between the two measuring points. By calculating the gas composition change for successive measuring points for each breath included in the measurement and by calculating an average of these changes between the measuring points and over the breaths, an average signal characteristic breath pattern or profile can be composed by starting from an initial reference value and adding the average changes to this reference value. Any number of breaths can be included in the average breath calculation. The reference value can be an average gas concentration of all breaths at a base volume. The average changes are calculated using only the breaths having a maximum volume larger than or equal to the volume for which the average change is calculated. At each volume, only the breaths meeting this requirement are included in the average change calculation. The average breath pattern so formed is free from distortions present in ordinary averaging, such as those shown in FIG. 1.

DETAILED DESCRIPTION

Figure 2:
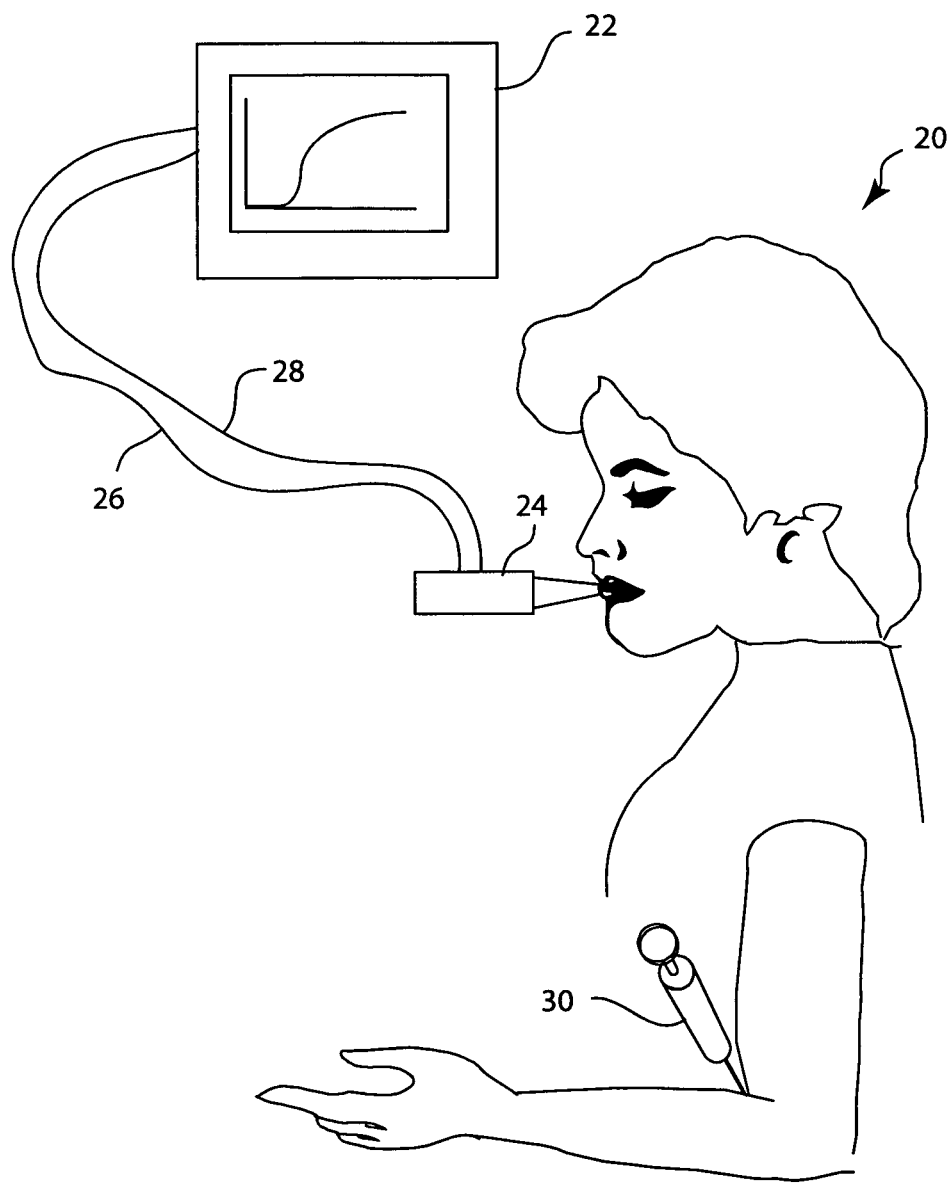
FIG. 2 shows apparatus of the present invention for making a measurement for a volumetric capnography curve and apparatus for arterial blood sampling.

Apparatus for obtaining the signals needed for volumetric capnography (VCap) is shown in FIG. 2. The breathing gas composition is measured with any type of fast response equipment for sensing the $CO_2$ properties of the breath pattern of patient 20. This may typically include an analyzer using infrared absorption, or a chemical analyzer, for $CO_2$. The sensor for the analyzer can be located within the measuring device 22 or at mouthpiece 24 through which patient 20 breaths. In the former case, the analyzer is of the side-stream type in which a gas sample is drawn through a sample line 26 for analysis. In the latter case, the gas analyzer is of the main-stream type in which the gas composition is analyzed directly from the breathing gases.

Breathing gas volume can be measured by integration of a flow signal over time using a breathing gases flow sensor located in mouthpiece 24. For flow measurement, any known type of flow sensor, including thermal, ultrasonic, and pressure difference sensors can be utilized. A pressure difference sensor may use e.g. a flow restrictor or pitot-tube to create the flow dependent pressure signal. The flow sensor signal is transferred through the signal transfer line 28 to the measuring device 22.

Arterial blood is sampled into a syringe 30 e.g. from an artery of patient 20. Typically, an artery in the arm is used for this purpose. The blood gas quantities are determined in a blood gas analyzer, not shown.

Figure 3:
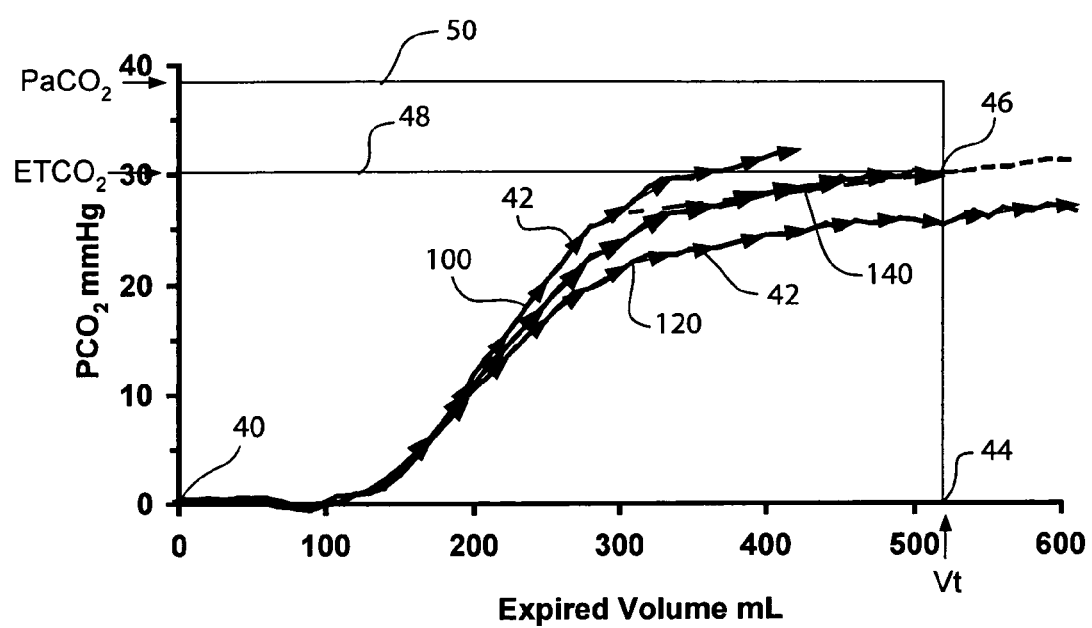
FIG. 3 presents data for the same breaths shown in FIG. 1 but which have been subjected to the method of the present invention and shows an average signal characteristic profile obtained with the method of the invention.
Figure 4:
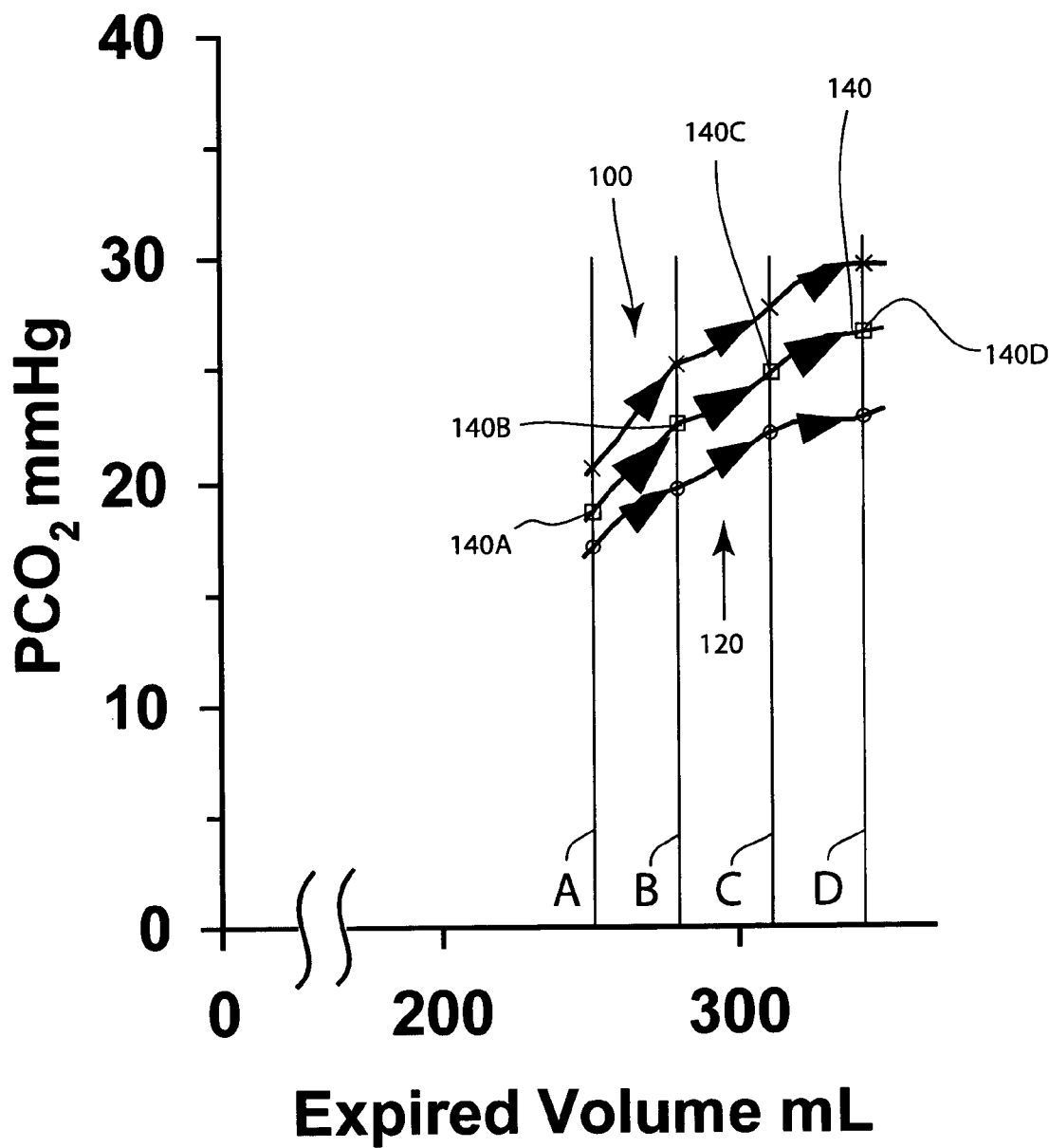
FIG. 4 is an enlarged view of a portion of FIG. 3 showing the manner in which the average signal characteristic profile is determined by the method of the present invention.

FIGS. 3 and 4 present the same simplified example explained above in connection with FIG. 1 to show how an averaged signal representing a characteristic profile of a cyclical signal is formed by the practice of the present invention.

Although the present description exemplarily, for reasons of simplicity, presents the method using only two breaths 100 and 120, the number of breaths employed can be any number greater than one. Advantageously for the purpose of forming an appropriate VCap curve for comparative and diagnostic purposes, all breaths occurring during collection of the arterial blood sample are included in composing the average signal characteristic profile.

Sampling of the breaths to be used in the method of the present invention begins from a reference point, which in FIG. 3 is the beginning of expiration at zero volume, or at point 40. Reference point 40 may also be any other well-defined point in a breath or breaths. The expired gas $CO_2$ concentration at the reference point is calculated as average of all breath values at this point. In the example shown in FIG. 3, this would be a zero concentration for each breath.

Further $CO_2$ samples are taken as the expiration proceeds, i.e. as the expired breathing gases volume moves to the right along the abscissa of FIG. 3. The sampling may occur at constant or variable intervals, and corresponding reference axis values starting from the reference point. The sampling for each breath is carried out at similar abscissa values, that is, at the same expired breathing gas volumes.

Respective changes along the ordinate, which is breathing gases $CO_2$ concentration expressed as partial pressure in FIG. 3, are calculated between two successive samples for each breath 100, 120 as the difference between the two samples. As shown more clearly in the enlarged view of FIG. 4, the changes between two successive samples are expressed with arrows 42.

In the method and apparatus of the present invention, an average expiration profile is formed starting from the reference point value 40, by adding the average changes in the values for breaths 10 and 12 to an average value at a previous point. Upon reaching the maximum abscissa value of any breath participating in the average change calculation, the method excludes this breath from further averaging, and the averaging continues among only the remaining breaths. Specifically, the average change calculation is shown in FIG. 4 of the drawing. FIG. 4 shows the ordinate of FIG. 3 and a portion of the abscissa around 300 ml of expired breathing gases volume along with portions of the data curve for breaths 100 and 120. Four successive sampling points A, B, C, and D are shown.

To carry out the method of the present invention, the change in breathing gases $CO_2$ partial pressure ($PCO_2$) for breaths 100 and 120 is calculated between successive samplings. For example, the change in $PCO_2$ for breath 100 between sampling points A and B is about 4 mmHg and for breath 12 about 3 mmHg. The average change for breaths 100 and 120 would be 3.5 mmHg.

In determining the profile 140 for the patient's expired breathing gases, the amount of 3.5 mmHg would be added to a reference value 140A established at sampling point A of about 19 mmHg, to produce a new value for the profile point 140B of about 22.5 mmHg for the average characteristic profile curve 140. The same procedure is carried out in an analogous manner for sampling points B and C and sampling points C and D produce points 140C and 140D on curve 140.

This procedure may be continued up to the largest expiration volume of any breath included in the averaging, i.e. the tidal volume $V_T$ and a continuous curve 140 is formed that accurately reflects the $PCO_2$ characteristics of both breaths 100 and 120, as shown in FIG. 3, even though the expired volume of one breath, breath 100, is less than that of another breath, breath 120.

Figure 1:
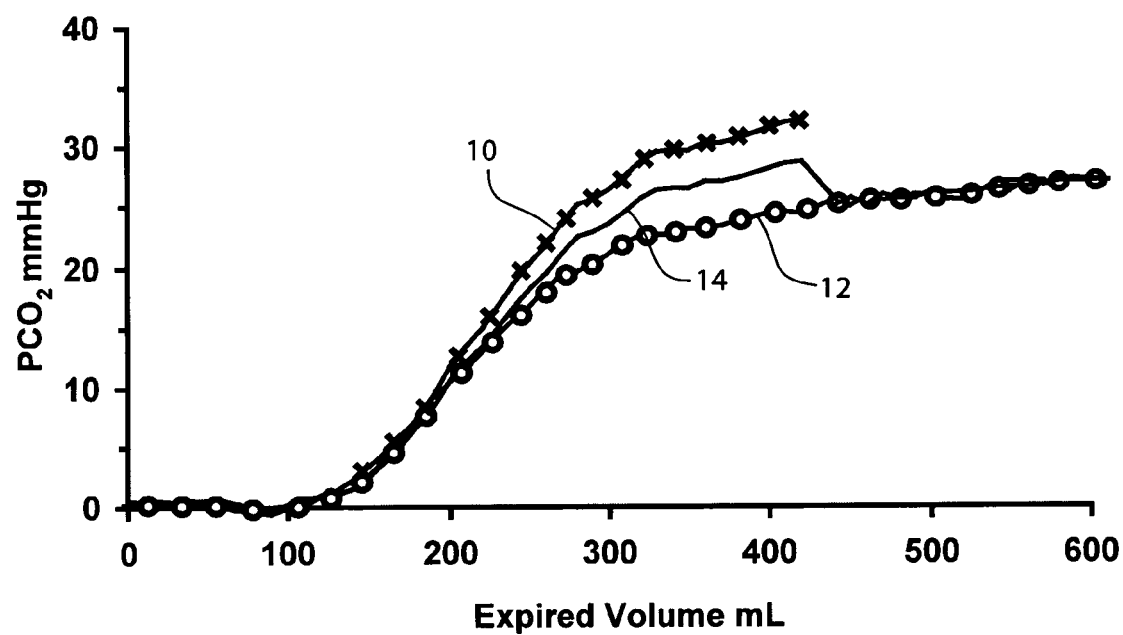
FIG. 1 is a graph showing two individual breaths sampled at equal volume intervals and also showing a graph composed by averaging the equivolumic values of the individual breaths.

Over a period of time, average tidal volume $V_T$ determines lung ventilation. Therefore, the average characteristic curve 140 is advantageously continued up to the average of the tidal volumes of the individual breaths. This is point 44 in FIG. 3 as determined by the volume scale abscissa distance between the VCap start- and end-points. In FIGS. 1 and 3, the expiration start is nominated as zero volume, thus the VCap endpoint 44 projection on the volume scale defines the tidal volume. For breaths 10 and 100, the tidal volume end point is 430 ml. For breaths 12, 120, the tidal volume end point is 600 so the average tidal volume is 515 ml as shown in FIG. 3 by 44. The end-tidal $CO_2$ concentration obtained by carrying out the technique of the present invention is the end-point $CO_2$ concentration 46 of the VCap curve at volume $V_T$ 44, as shown by line 48 projected to the ordinate, and is about 30 mmHg.

As illustrated in FIG. 3, the breath 100 ends at the tidal volume end point of 430 ml while the second breath 120 ends at the tidal volume end point of 600 ml. The average VCap curve 140 is calculated between pairs of successive sampling points as the average change between the sampling points for the breaths 100 and 120 at all of the sampling points below the tidal volume end point for the smaller breath 100. For sampling points below the tidal volume of the smaller breath 100, both breaths 100 and 120 have measured values for $PCO_2$ at both of the pair of successive first and second data points. The system and method of the present invention determines the amount of change between successive sampling points for each of the two breaths 100 and 120 and determines an average change between the successive first and second data points. This average is added to the reference value established at the first data point to create the reference value at the second data point.

In the method and apparatus of the present invention, at successive sampling points following the tidal end point of breath 100, only the second breath includes a $PCO_2$ value. Since no physiological property value is present for the first breath, the method and apparatus of the present invention utilizes only the change in $PCO_2$ of the breath 120 that includes the $PCO_2$ at both of the air of successive data points as the average change amount. Thus, as can be seen in FIG. 3, the average characteristic curve 140 follows the breath 120 for data points following the tidal volume end point for breath 100. Thus, contrary to the prior art system shown in FIG. 1, the average characteristic curve 140 does not automatically track with the larger breath and instead utilizes only the change in the second physiological property of the larger breath.

The slope of the profile for the alveolar portion of expiration, from about 325 mL of expired volume on, determined from the average VCap curve 140 now expresses correctly the true alveolar V/Q profile. Comparison to the $PaCO_2$ analyzed from the blood sample during the recording of the breaths used for formation of the average VCap characteristic profile and indicated by line 50 in FIG. 3 gives a full picture of the V/Q relationship of the lung.

Various alternatives and embodiments are contemplated as being within the scope of the following claims particularly pointing out and distinctly claiming the subject matter regarded as the invention. For example, while the present invention has been described using the physiological functioning of the lungs as an example of a cyclic process, it could be used with other cyclic processes such as those associated with the functioning of the heart. And, it can also be used in connection with the measurement of other components of a subject's breathing gases besides $CO_2$, such as oxygen or nitrous oxide.

What is claimed is:

1. A method for providing an average signal characteristic profile relating first and second physiological properties, the average signal characteristic profile being derived from signals obtained from different cycles of a cyclically recurring physiological phenomenon, said method comprising the steps of:
   (a) sampling the signal produced from a first cycle of the physiological phenomenon at a series of data points of a first physiological property to obtain second physiological property values of the first cycle signal at the data points;
   (b) sampling the signal produced from a second cycle of the physiological phenomenon at a series of data points corresponding to those of the first series of data points to obtain second physiological property values of the second cycle signal at the data points;
   (c) determining the change in the second physiological property values for the first cycle signal between a pair of successive data points including a first data point and a second data point;
   (d) determining the change in the second physiological property values for the second cycle signal between the same pair of successive first and second data points;
   (e) averaging the determined amount of change of only the cycle signals having second physiological property values at both of the pair of successive first and second data points to produce an average change amount between the successive first and second data points;
   (f) utilizing only the change in the second physiological property of the first or second cycle signals having the second physiological property value at both of the pair of successive data points as the average change amount when the other of the first and second cycle signals does not have the second physiological property value at both of the pair of successive data points; and
   (g) adding the average change amount to a value of the average signal characteristic profile at the first of the pair of successive data points to produce a new second physiological property value for the average signal characteristic profile at the second of the data points of the pair of successive data points.

2. A method according to claim 1 further defined as repeating steps (c), (d), (e), (f) and (g) for at least one additional pair of data points to provide at least one additional new second physiological property value for the average signal characteristic profile.

3. A method according to claim 1 further including the steps of: sampling the signal produced from at least one additional cycle of the physiological phenomenon in the manner described in step (b); determining the change in the physiological phenomenon values in the additional cycle signal between the pair of successive data points; averaging the amounts of change in the sampled cycle signals to produce an average change amount for the successive data points; and applying the average change amount to a value of the average signal characteristic profile in the manner described in step (g).

4. A method according to claim 3 further defined as repeating steps (c), (d), (e), (f) and (g) for at least one additional pair of data points to provide at least one additional new second physiological property value for the average signal characteristic profile.

5. A method according to claim 1 further defined as a method for providing an average signal characteristic profile for a physiological phenomenon comprising breathing.

6. The method according to claim 5 further defined as providing an average signal characteristic profile relating desired physiological properties of the expirations of the breaths of a patient.

7. A method according to claim 6 further defined in that the first physiological property is expired breathing gas volume and the second physiological property is expired amounts of $CO_2$.

8. A method according to claim 7 further including the steps of obtaining a measurement of the arterial blood $CO_2$ amounts in the blood of the patient and as carrying out the steps of claim 1 for breaths occurring during the blood sampling.

9. The method according to claim 7 wherein expirations end at a tidal volume for each breath and wherein the method further includes the step of averaging the tidal volumes for the breaths and the step of establishing the $CO_2$ value characteristic at the average tidal volume as the amount of $CO_2$ in the lungs of the patient at the end of expiration.

10. The method according to claim 9 further including the steps of obtaining a measurement of the arterial $CO_2$ amounts in the blood of the patient and the step of comparing the arterial blood $CO_2$ amount to the amount of $CO_2$ in the lungs of the patient at the end of expiration.

11. The method according to claim 7 further defined as including the step of establishing a reference value to which the average change amount may be applied as the average of the values of the second physiological property for the cycle signals at a breathing gas base volume.

12. The method according to claim 6 wherein expirations end at a tidal volume for each breath and wherein the method further includes the step of averaging the tidal volumes for the breaths.

* * * * *